United States Patent [19]
Billings et al.

[11] Patent Number: 5,324,288
[45] Date of Patent: * Jun. 28, 1994

[54] ELECTROSURGICAL LOOP WITH A DEPTH GAUGE

[75] Inventors: R. Gail Billings, Holladay; William D. Wallace, Salt Lake City; Christopher A. Cutler, Centerville; B. Tod Cook, Sandy; Jon N. Neese, Holladay, all of Utah

[73] Assignee: Utah Medical Products, Inc., Salt Lake City, Utah

[*] Notice: The portion of the term of this patent subsequent to Nov. 3, 2009 has been disclaimed.

[21] Appl. No.: 693,529

[22] Filed: Apr. 30, 1991

[51] Int. Cl.$^5$ .............................. A61B 17/39
[52] U.S. Cl. ..................... 606/45; 606/172; 606/32; 606/39; 606/47
[58] Field of Search ............. 606/27, 28, 32, 37, 606/39, 45, 46, 47, 48, 167, 170, 172, 107, 113; 604/22

[56] References Cited

U.S. PATENT DOCUMENTS

| | | | |
|---|---|---|---|
| 1,930,214 | 10/1933 | Wappler | 606/46 |
| 4,311,143 | 1/9182 | Komiya | 606/47 |
| 4,534,348 | 8/1985 | Federov et al. | 606/172 X |
| 4,552,146 | 11/1985 | Jensen et al. | 606/172 X |
| 4,682,597 | 7/1987 | Myers | 606/172 |
| 4,750,489 | 6/1988 | Berkman et al. | 606/172 X |
| 4,759,363 | 7/1988 | Jensen | 606/172 |
| 4,869,248 | 9/1989 | Narula | 606/45 |
| 5,160,334 | 11/1992 | Billings et al. | 606/34 |

OTHER PUBLICATIONS

*Contemporary OB/GYN*, Mar. 1991, vol. 36, No. 3, pp. 57-73, T. C. Wright, Jr., M.D. et al., "Excising CIN lesions by loop electrosurgical procedure."
*Obstetrics & Gynecology*, May 1990, vol. 75 No. 5, pp. 884-885, Shlomo Mor-Yosef, M.D. et al., "Instruments & Methods -Loop Diathermy Cone Biopsy".
*British Journal of Obstetrics and Gynaecology*, Sep. 1989, vol. 96, pp 1054-1060, "Large loop excision of the transformation zone (LLETZ)."

*Primary Examiner*—Peter A. Aschenbrenner
*Attorney, Agent, or Firm*—Madson & Metcalf

[57] ABSTRACT

An electrosurgical loop comprising an insulated shaft with an electrical contact at its proximate end and a pair of extending insulated prongs at its distal end. The extending prongs are configured to give the loop a "Y" shape and each end of a thin wire are connected to each prong to provide a wire loop. Disposed over the shaft in longitudinal sliding engagement is a depth gauge comprising a clasp, a longitudinal intermediate portion, and a transverse cross bar. The clasp may be retrofit to an existing electrosurgical loop and permits the removal of the depth gauge from the loop, if desired. The transverse cross bar is wider than the breadth of the wire loop and has a transverse slot oriented in the same plane as the wire loop through which the wire loop passes as the depth gauge is adjusted for various cutting depths. Disposed on the insulated shaft are markings serving as depth indicators to which the depth gauge may be moved slidably to effect cut depth control for the loop. The loop may be constructed by punching a series of shaft blanks from a conductive metal stock, and rolling the electrical contact prior to applying the insulation. Also, prior to applying the insulation, the wire loop can be connected to the shaft blank to maintain the flow of electrical current through the shaft into the wire loop.

23 Claims, 4 Drawing Sheets

ELECTROSURGICAL LOOP WITH A DEPTH GAUGE

FIELD OF THE INVENTION

The present invention relates to an apparatus used for performing electrosurgical excision procedures, and more particularly to an electrosurgical loop having a depth gauge for assisting in depth limitation during excision.

BACKGROUND OF THE INVENTION

In recent years there has developed an increased incidence of cervical intraepithelial neoplasia (CIN), i.e., sexually transmitted genital warts. Since the majority of cases occur in women of reproductive age who have not completed their families, conservative treatment has been advisable.

Management procedures using electrocoagulation, electrodiathermy, cryosurgery and laser surgery are accepted but each such procedure has drawbacks and all require considerable skill and experience. Cold knife and laser surgery typically require hospitalization and general anesthesia. Using these procedures, there are occasions when the practitioner will miss invasive cancers or inadvertently treat cancers with ablative therapy.

Recently, loop electrosurgical excision procedures (LEEP) and large loop excision of the transformation zone (LLETZ) using thin wire electrodes have been used to treat CIN. These electrosurgical techniques can be provided on an outpatient basis under either local or general anesthesia. Also, these electrosurgical techniques have the advantage over other destructive techniques in that the specimen excised is not destroyed, but preserved for examination histologically. Additionally, microinvasive and invasive disease can be excluded and the limits of the lesion are clearly defined.

In performing these electrosurgical techniques, the loop is used with a monopolar generator (the "electrosurgical unit") which produces a number of waveforms for electrosurgical cutting and coagulation. In monopolar electrosurgery, a radio frequency current is passed through the body of the patient between an active electrode, where the current is very concentrated, and a disperse electrode, where the current is quite diffuse. The loop acts as the active electrode and is used as a cutting tool at the surgical site. The loop comprises an insulated shaft connected to insulated extending arms to which a loop wire is attached. The loop is connected to and is controlled by either a hand switch or a foot switch connected to the electrosurgical unit. The dispersive electrode is applied to the patient's body at a site away from the surgical field. Its purpose is to complete the electrical circuit and disperse the current returning to the electrosurgical unit.

Electrosurgery results from the concentration of electrical energy in tissue of the patient to the point that local tissue is destroyed or modified. In electrosurgical cutting, the cells conducting the concentrated current are heated to where the water contained within the cells boils causing the cells to explode and release the resulting steam. In electrosurgical coagulation, cells near the surface exposed to the concentrated current are heated so that they dehydrate and shrink, rather than explode, thereby closing open vessels.

To obtain cutting with a minimal heating, the electrosurgical unit drives the mall-wire loop with a continuous, unmodulated waveform. Cutting with shallow surface coagulation is obtained by modulating the cutting power source. This is known as a blended source. Typical electrosurgical units have a pure cut mode and multiple (usually three) blend modes. These blend modes use waveforms comprising bursts of radio frequency energy with smaller duty cycles causing greater coagulation activity and less cutting activity.

To obtain coagulation without cutting, typically an active electrode with larger cross section is used with the power source supplying an interrupted waveform. Two forms of coagulation are desiccation and fulguration. Desiccation coagulation is accomplished using a blunt active electrode, a coag or high blend waveform, and relatively low power. The less concentrated current dries and shrinks the affected cells causing a deeper penetration of thermal modification to the cells than is accomplished using a blend mode during cutting or by fulguration. Fulguration coagulation is accomplished using either a blunt or fine electrode with a coag mode waveform at high power. The active electrode is kept slightly spaced from the surface to be coagulated so that sparks jump across the gap. The surface area contacted by and the current from each spark is small so that the resulting thermal modification is shallow.

To avoid electrical shock to the patient caused by the depolarization of nerve or muscle cells by a non-physiologic electric voltage, frequencies above 300 kHz are used. To avoid electrical burns, the dispersive electrode must be carefully applied and care must be taken that the patient avoid metallic contacts. Further, the surgeon handling the active electrode must avoid applying it to his or her own body or touching it to any conductive tool or appliance.

Typically, a patient with an abnormal smear obtained during a colposcopic examination is identified as a candidate for an electrosurgical excision procedure using a loop. At the beginning of the procedure, routine colposcopy is performed using acetic acid and iodine to outline the cervical lesion. The patient is anesthetized and the dispersive electrode is applied.

After the patient has been prepared as briefly set forth above, the hand or foot control is activated thereby activating the loop. Using a slight downward pressure, the loop is pushed into the cervical tissue perpendicular to the surface as deeply as needed, but not too deeply. The loop is then advanced slowly across the cervix underneath the transformation zone and then withdrawn perpendicular to the surface of the cervix. The entire excision takes only about 5 to 10 seconds. The excised specimen is then removed for examination. After the excision, a diathermy ball operated at the coagulation mode is used to coagulate the cervical wound.

Electrosurgical excisions using a loop have several advantages over other procedures using a laser, cold knife, or cryogenic techniques. The tissue is removed rather than destroyed so that the entire transformation zone may be sent for histological examination. This minimizes the possibility of missing invasive disease. Additionally, the procedure may be performed at a patient's first visit to a colposcopy clinic, thereby affording valuable time savings to the patient and the colposcopy clinic.

Although the procedure for electrosurgical excision using a loop which has been described briefly above has marked advantages, there is a serious precaution that must be followed during the procedure. Precaution must be taken not to cut too deeply into the cervix. A range of depths from 5 to 8 mm is the preferred depth for the cut. Despite the inherent dangers of cutting too deeply and the speed with which the loop cuts readily through tissue, the depth of the cut has heretofore been left to the skill and experience of the surgeon. However, as the procedure becomes more widely known and practiced, surgeons having less experience with the technique are using it on their patients.

Hence, it would be a substantial contribution to electrosurgical excision using a loop if an improved apparatus and method for gauging the depth of the cut could be provided. It would be a further advance in the art if the apparatus could be used on a loop that optimizes the ability of the surgeon to visually observe the cut. The present invention provides such an apparatus and method.

OBJECTS AND BRIEF SUMMARY OF THE INVENTION

In view of the foregoing needs and problems experienced by surgeons performing electrosurgical excisions using a loop, it is a primary object of the present invention to provide a depth gauge for limiting the depth of the cut to a predetermined depth.

It is another object of the present invention to provide an apparatus wherein the depth gauge is adjustable within a range of acceptable depths.

A further object of the present invention is to provide a loop that can be used while optimizing the surgeons visual field.

Still another object of the present invention is to provide an apparatus that provides protection from accidental contact of the loop wire with the vaginal wall.

Yet another object of the present invention is to provide a depth gauge that can be retrofit to an existing electrosurgical loop.

Another object of the present invention is to provide a loop that can be manufactured easily and inexpensively.

The foregoing objects ar accomplished by an apparatus of the present invention which provides adjustable depth control while optimizing the surgeon's visual field during the performance of electrosurgical excision procedures.

One preferred embodiment of the present invention includes an electrosurgical loop comprising an insulated shaft with an electrical contact at its proximate end and a pair of extending insulated prongs at its distal end. The extending prongs are configured to give the loop a "Y" shape and each end of a thin wire are connected to each prong to provide a wire loop. Disposed over the shaft in longitudinal sliding engagement is a depth gauge comprising a clasp, a longitudinal intermediate portion, and a transverse cross bar. The clasp is of a type which permits the removal of the depth gauge from the loop, if desired. The transverse cross bar is wider than the breadth of the wire loop and has a transverse slot oriented in the same plane as the wire loop through which the wire loop passes as the depth gauge is adjusted for various cutting depths. Disposed on the insulated shaft are markings serving as depth indicators to which the depth gauge may be moved slidably to effect cut depth control for the loop.

In another embodiment of the present invention the transverse cross bar is flat and does not have a transverse slot. With this embodiment the cross bar is disposed adjacent the wire loop, but does not encircle the wire loop in the manner that the slotted cross bar does.

With either embodiment of the cross bar, the cross bar is constructed of a non-conductive material with a degree of rigidity necessary to withstand, without sliding movement, the minimal pressure that the cervical wall may apply to the cross bar during the excision procedure. Preferably, the cross bar is made of a transparent material to minimize any negative effect the depth gauge may have on the surgeon's vision of the surgical field.

The loop of the present invention may be constructed by punching a series of shaft blanks from a conductive metal stock, and rolling the electrical contact prior to applying the insulation. Also, prior to applying the insulation, the thin wire used to make the wire loop can be connected to the shaft blank by spot welding or any of a number of suitable means of connection that will maintain the flow of electrical current through the shaft into the wire loop.

These and other objects and features of the present invention will become more fully apparent through the following description and appended claims taken in conjunction with the accompanying drawings.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

Figure 1:
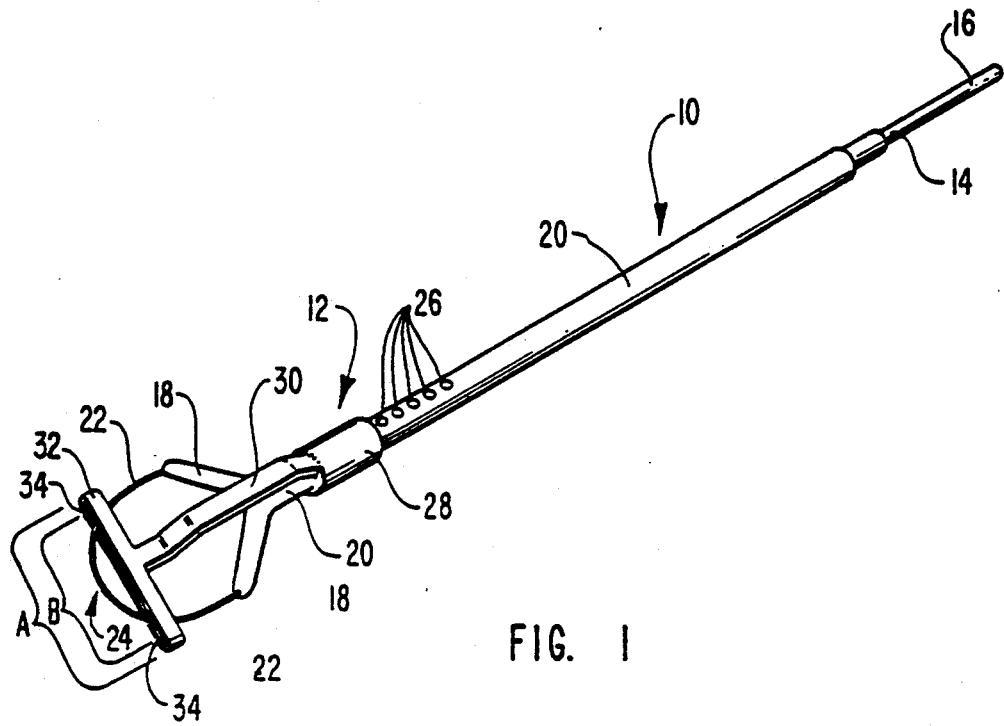
FIG. 1 is perspective view of the present invention showing the loop with the depth gauge in slidable engagement therewith.

Referring now specifically to the drawings, wherein like numerals indicate like parts throughout, one preferred embodiment of the present invention, as best shown in FIG. 1, includes an electrosurgical loop generally designated 10 and a depth gauge generally designated 12.

The electrosurgical loop 10 comprises a shaft 14 with an electrical contact 16 at its proximate end and a pair of extending prongs 18 at its distal end. Except for the electrical contact 16, the entire length of the shaft 14 is covered with an insulation 20 made of a non-conductive material such as plastic. The extending prongs 18 are configured to give the loop 10 a Y-shape and each end of a thin wire 22 are oonneoted to each respective prong 18 to provide a wire loop, generally designated at 24. Disposed on the insulated shaft 14 are markings 26 serving as depth indicators to which the depth gauge 12 ma be moved slidably to effect cut depth control for the loop 10.

Figure 2:
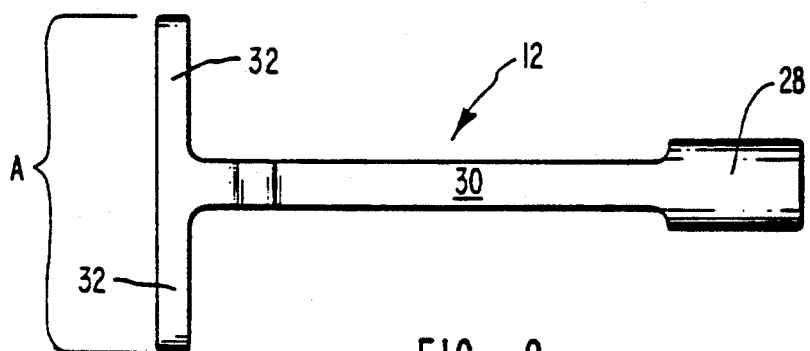
FIG. 2 is top plan view of one preferred embodiment of the depth gauge.
Figure 3:
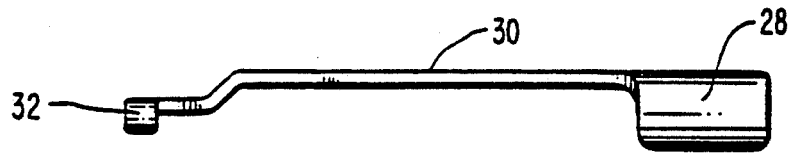
FIG. 3 is an elevational side view of the depth gauge shown in FIG. 2.
Figure 4:
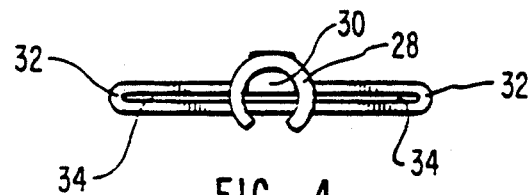
FIG. 4 is an elevational end view of the depth gauge of the present invention showing the clasp and the transverse slot formed in the cross bar.

The depth gauge 12 is disposed over the insulation 20 of shaft 14 in longitudinal sliding engagement, and comprises a clasp 28, a longitudinal intermediate portion 30, and a transverse cross bar 32. As shown best in FIGS. 2 through 4, the clasp 28 is of a type which permits sliding along the insulated shaft 14 and also permits the removal of the depth gauge 12 from the loop 10, if desired. Of course, it is contemplated to be within the spirit and scope of the present invention that the depth gauge 12 can be made in various sizes so that it can be retrofit to existing electrosurgical loops 10, thereby providing depth control and added safety to the use of the loop 10.

Although a clasp 28 of a "C" shaped cross section is shown, it should be understood that other configurations for the clasp 28 may be used. For example, a clasp 28 with a full circular cross section can be used suitably, as well as other clasp configurations.

The transverse cross bar 32 is wider (indicated by bracket A) than the breadth of the wire loop 24 (indicated by bracket B) and has a transverse slot 34 oriented in the same plane as the wire loop 24 through which the wire loop 24 passes as the depth gauge 12 is adjusted for various cutting depths. (See FIG. 1). Although very little or no support is needed for the thin wire 22 during the excision procedure, if properly performed, the transverse cross bar 32 can provide support for the thin wire 22 for any drag of the wire 22 as it passes through the tissue.

The Y-shaped configuration of the shaft 14 and prongs 18 optimizes the field of vision for the surgeon using the loop 10 during electrosurgery in that the area near the crotch of the "Y" is unobstructed. It should be understood; however, that the depth gauge 12 of the present invention can be adapted to be used on or retrofit to loops 10 having configurations different than a Y-shape, for example, "T" shaped and "U" shaped loops are known and could be used with little or no adaptation required. All such loop 10 configurations are considered to be within the spirit and intended scope of the present invention.

In addition, it is preferred that the depth gauge be constructed of a non-conductive material such as plastic that is transparent. Although, such material is preferred, other non-conductive materials may be used that may or may not be transparent. Additionally, the depth gauge 12 may be constructed of a material which can be sterilized so that the depth gauge is reusable.

Further, it is contemplated that the insulation 20 is injection molded about the shaft 14 and prongs 18 in a manner that is commonly known in the industry. However, it should be understood that the insulation may be applied by any means so long as it insulates the portion of the loop 10 device which may come into contact with the surgeon's hand or undesired portions of the patient's body.

Figure 5A:
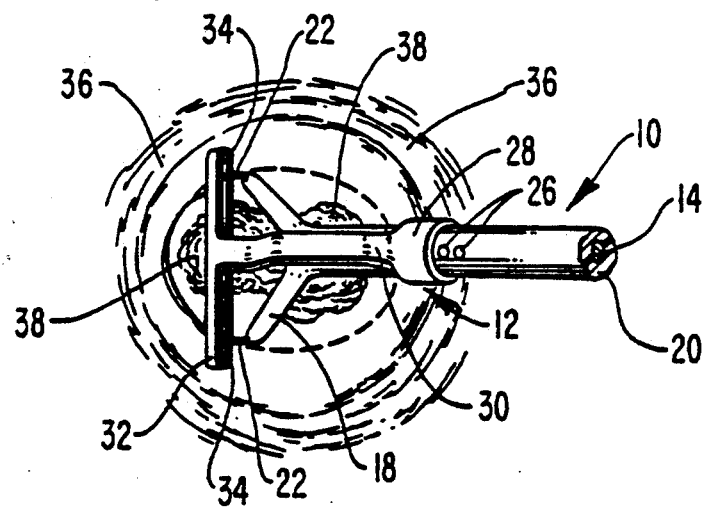
FIG. 5A is a perspective view illustrating the loop and depth gauge of the present invention in use during early stages of an electrosurgical excision of a cervical lesion.
Figure 5B:
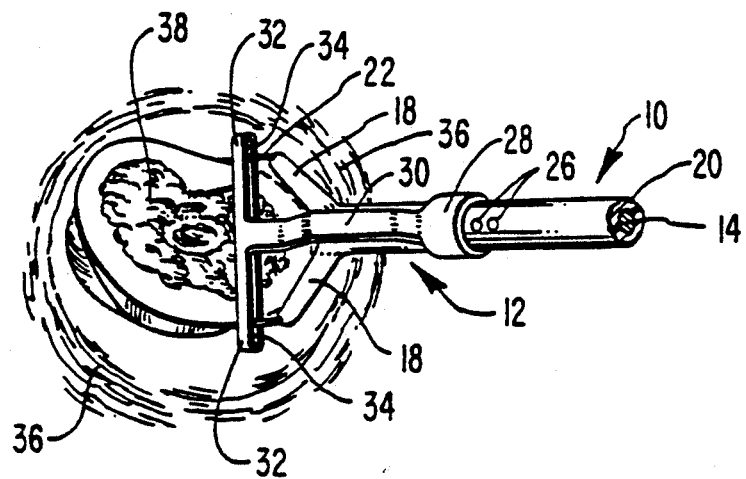
FIG. 5B is a perspective view similar to that of FIG. 5A during a more advanced stage of the electrosurgical excision procedure.
Figure 5C:
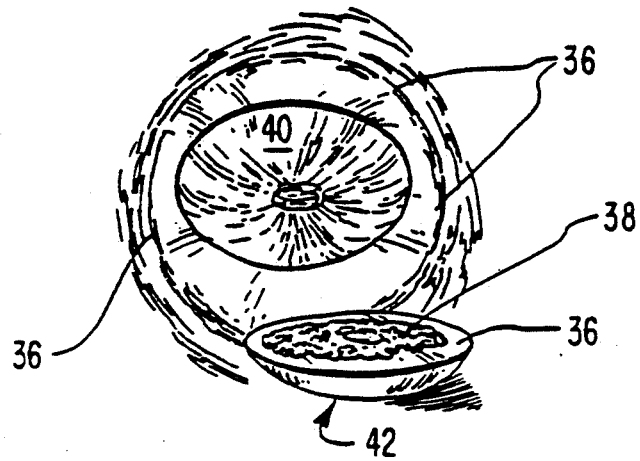
FIG. 5C is a perspective view of the excision bed in a cervical wall after electrosurgical excision with the excised specimen disposed adjacent thereto.

Turning now to FIGS. 5A, 5B, and 5C, the use of the present invention during electrosurgical excision of a cervical lesion will be briefly explained. FIG. 5A illustrates the loop 10 and the depth gauge 12 of the present invention during the early cutting stages of an electrosurgical excision. As can be seen, the thin wire 22 of wire loop 24 enters the cervical wall 36 at a point slightly removed from the lesion 38 (also known as the transformation zone). The wire loop 24 is advanoed underneath the lesion 38 along the path designated by the phantom lines of FIG. 5A. The depth of the cut is controlled by the presurgical selection of depth and placement of the depth gauge 12 according to the desired marking 26. FIG. 5B shows a more advanced stage of the electrosurgical excision wherein the wire loop 24 is clearly beneath the lesion 38. FIG. 5C illustrates the cervical wall 36 and the bed of the cervical wound 40 after the excision is complete, it further illustrates a specimen 42 of cervical wall 36 containing the lesion 38 which can now be forwarded for histological examination.

Although operation of the loop 10 and depth gauge 12 of the present invention is described in a CIN excision procedure, it should be understood the loop lo together with the depth gauge 12 can be used in other electrosurgical procedures, vulval, vaginal, perianal, and the removal of penile lesions for example. Use in other procedures may require slight modifications to the size of the loop 10 and depth gauge 12 to accommodate the procedure.

Further one of the primary advantages of the present invention is to provide for a surgeon that is relatively inexperienced in electrosurgical excisions the safety provided by the depth gauge 12. The depth gauge 12 controls the depth of the cut according to a predetermined setting made by the surgeon, thereby eliminating an overly deep cut due to the inexperience of the surgeon. Cuts that are made too deeply bleed readily and heal less readily than shallower cuts. Also, since the transverse cross bar 32 extends beyond the lateral reach of the wire loop 24, the cross bar 32 shields the vaginal or cervical wall from inadvertent contact with the sides of the wire loop 24. This significantly reduces misplaced and inadvertent cuts in the tissue of the patient. As the practitioner develops experience in performing the procedure, the depth gauge 12 may be removed to increase the visibility of the surgical field, or the practitioner may choose to leave the depth gauge 12 in place for safety purposes.

Figure 6:
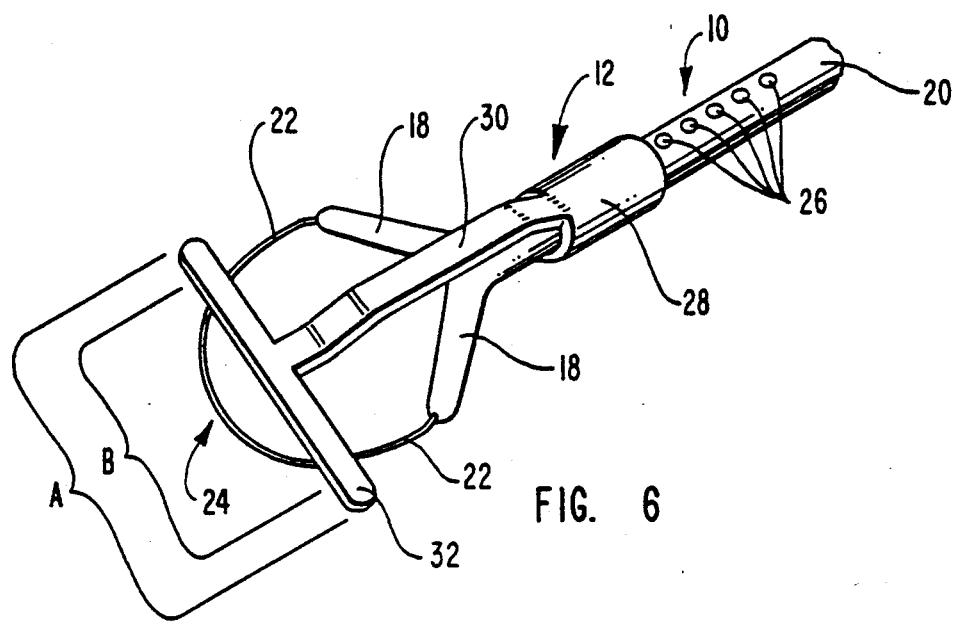
FIG. 6 is a perspective view of an alternative preferred embodiment of the depth gauge disposed on a loop.

An alternative embodiment of the depth gauge 12 of the present invention is illustrated at FIG. 6. With this embodiment, the depth gauge 12 comprises a clasp 28, an intermediate portion 30, and a transverse cross bar 32; however, the transverse cross bar 32 is flat and does not have a transverse slot 34. This embodiment is disposed in slidable engagement with the loop 10 so that the oross bar 32 lies adjacent the wire loop 24. The manner of operation of this alternative embodiment is virtually the same as with the previously described preferred embodiment, the cut depth is preselected by the surgeon by sliding the depth gauge 12 to the desired position and the excision is made using the depth gauge 12 to control the depth of the cut.

Figure 7A:
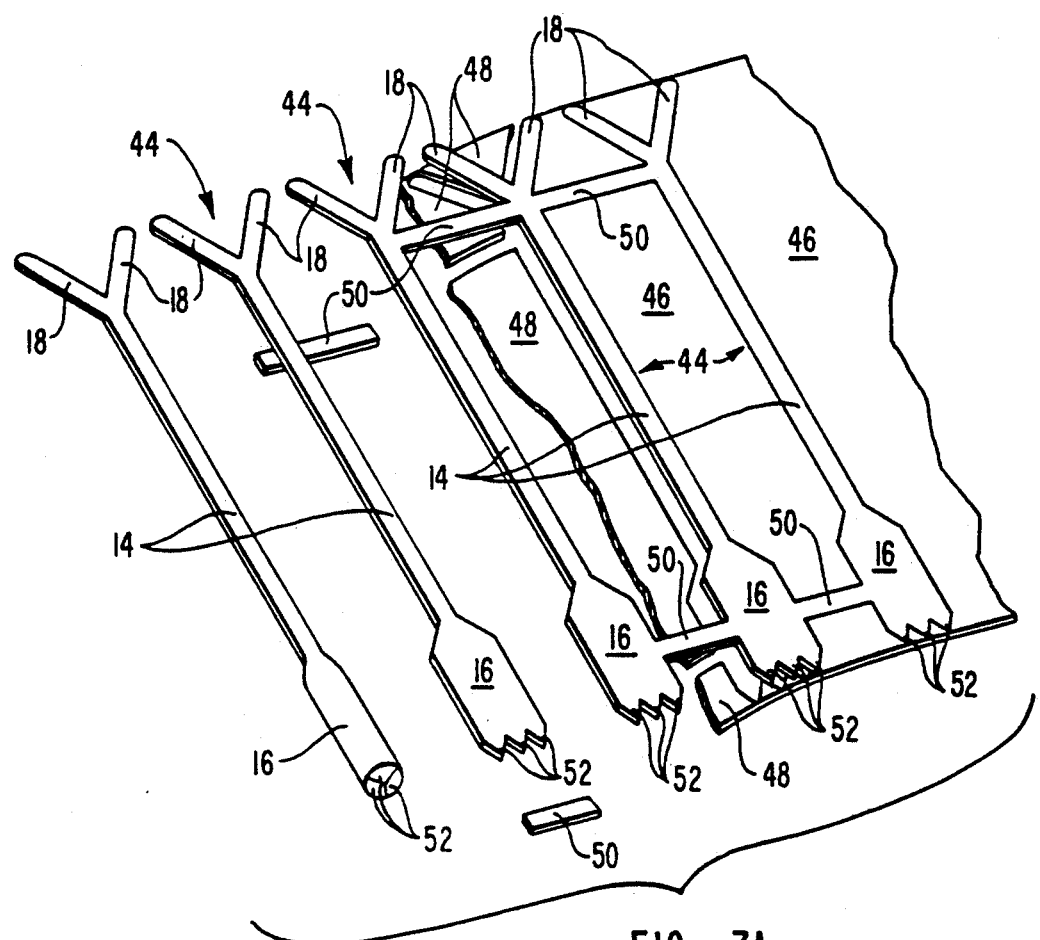
FIG. 7A is perspective progressive schematic of a shaft blank being punched from a metal sheet and rolled in preparation for applying insulation.
Figure 7B:
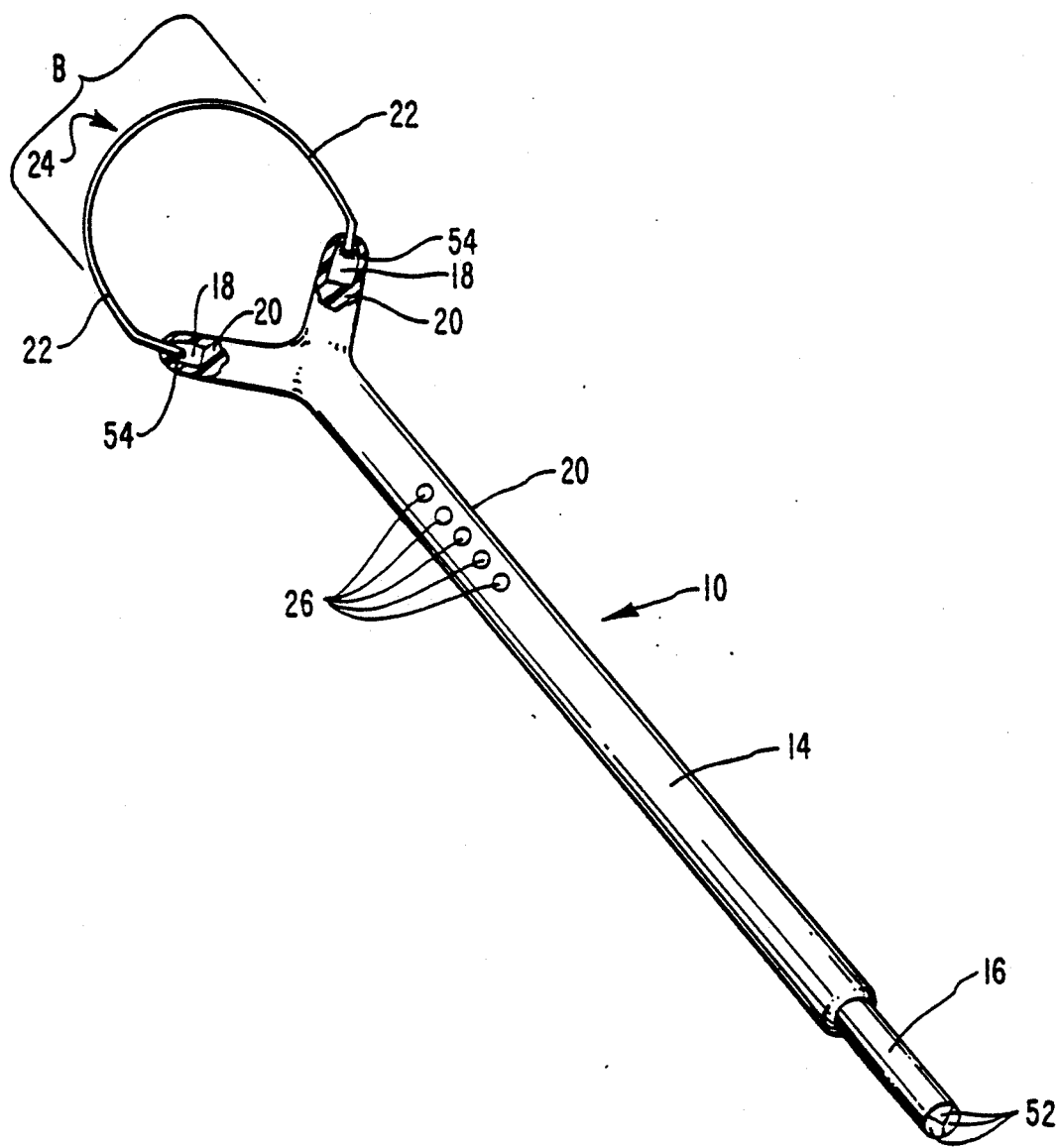
FIG. 7B is a perspective view of the loop of the present invention with a portion of the insulation cut away to show the thin wire spot welded to the shaft blank.

With reference now to FIGS. 7A and 7B, a preferred method for manufacturing the loop 10 of the present invention is illustrated. Loop 10 of the present invention may be constructed by punching a series of shaft blanks 44 from a conductive metal stock 46 as illustrated in FIG. 7A. The progressive steps of this procedure are illustrated as you move from right to left in FIG. 7A. First, the pattern can be marked on the stock 46 which is made of electrically conductive material. Second, a first punching of the stock 46 severs the shaft blanks 44 from the undesired portions 48 of the stock 46 leaving only connecting bridges 50 to join adjacent shaft blanks 44 in series. Third, the bridges 50 are removed once the shaft blank 44 has advanced to a position where the individual shaft blanks can be handled and maneuvered easily. Finally, the electrical contact 16 is rolled and pigtails 52 are bent inward to shape the electrical contact 16 for electrical connection to an electrosurgical unit (not shown).

The preparation of the shaft blanks 44 is performed prior to applying the insulation by injection molding or some other method of insulation application. Also, prior to applying the insulation, the thin wire 22 used to make the wire loop 24 can be connected to the shaft blank 44 by spot welding or any of a number of suitable means of connection that will maintain the flow of electrical current through the shaft 14 into the wire loop 24. The position of the spot welding or other suitable connection is designated at 54 in FIG. 7B.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An apparatus capable of electrical connection to na electrosurgical unit for performing electrosurgical excision, comprising:
   an electrosurgical loop comprising a shaft having a proximate end for connection to the electrosurgical unit and a distal end having a wire loop connected thereto; said wire loop being capable of electrical communication with the electrosurgical unit; and,
   a depth gauge means disposed in slidable engagement with said shaft for determining the amount of said wire loop exposed for making the excision by sliding said depth gauge means along said shaft.

2. An apparatus as set forth in claim 1, wherein said shaft further comprises a pair of extending prongs disposed at the distal end of said shaft to which said wire loop is connected and said prongs being capable of electrical communication with the electrosurgical unit.

3. An apparatus as set forth in claim 2, wherein said wire loop is connected to said prongs by spot welding.

4. An apparatus as set forth in claim 2, wherein said prongs are configured such that said prongs and said shaft form a Y-shaped configuration.

5. An apparatus as set forth in calim 1, wherein the proximate end of said shaft comprises an electrical contact configured for connection to the electrosurgical unit and the remainder of said shaft is covered with insulation.

6. An apparatus as set forth in claim 5, wherein said insulation is applied to said shaft by injection molding.

7. An apparatus as set forth in claim 5, wherein said electrical contact is formed by rolling a shaft blank.

8. An apparatus as set forth in claim 1, wherein said shaft further comprising markings for identifying a plurality of positions to which said depth gauge means may be slidably disposed.

9. An apparatus as set forth in claim 1, wherein said depth gauge means comprises a clasp means and a cross bar, said clasp means securing said depth gauge means in slidable engagement with said shaft, said cross bar being disposed adjacent said wire loop for defining the amount of wire loop exposed for excision.

10. An apparatus as set forth in claim 9, wherein said clasp means is configured to have a C-shaped transverse section.

11. An apparatus as set forth in claim 1, wherein said depth gauge means is removable from slidable engagement with said shaft.

12. An apparatus as set forth in claim 1, wherein said depth gauge means is constructed of plastic.

13. An apparatus as set forth in claim 1, wherein said depth gauge means is transparent.

14. An apparatus as set forth in claim 9, wherein said cross bar further comprises a slot disposed in the same plane as said wire loop such that said wire loop extends through said slot.

15. An apparatus as set forth in claim 9, wherein the transverse width of said cross bar is greater than the breadth of said wire loop, thereby providing a shield beyond the lateral reach of said wire loop.

16. An apparatus for controlling the depth of an electrosurgical excision cut made by an electrosurgical loop having a wire loop, comprising:
   a depth gauge means disposed in slidable engagement with the electrosurgcal loop for determining the amount of the wire loop exposed for making the excision by sliding said depth gauge means along the electrosurgical loop, said depth gauge means comprises:
   a clasp means for securing siad depth gauge means in slidable engagement with the electrosurgical loop; and
   a cross bar disposed adjacent the wire lop for defining the amount of wire loop exposed for excision.

17. An apparatus as set forth in claim 16, wherein said clasp means is configured to have a C-shaped transverse section.

18. An apparatus as set forth in claim 16, wherein said depth gauge means is removable from slidable engagement with the electrosurigcal loop.

19. An apparatus as set forth in claim 16, wherein said depth guage means is constructed of plastic.

20. An apparatus as set forth in claim 16, wherein said depth gauge means is transparent.

21. An apparatus as set forth in claim 16, wherein said depth gauge means is capable of retrofit to an existing electrosurgical loop.

22. An apparatus as set forth in claim 16, wherein said cross bar further comprises a slot disposed in the same plane as the wire loop such that the wire loop extends through said slot.

23. An apparatus as set forth in claim 16, wherein the transverse width of said cross bar is greater than the breadth of the wire loop, thereby providing a shield beyond the lateral reach of the wire loop.

* * * * *